(12) United States Patent
Bilyeu

(10) Patent No.: US 6,909,033 B1
(45) Date of Patent: Jun. 21, 2005

(54) SOYBEAN VARIETY S03-95341-A98-60618

(75) Inventor: Keith Bilyeu, Ames, IA (US)

(73) Assignee: Advanta U.S.A., Inc., Slater, IA (US)

( * ) Notice: Subject to any disclaimer, the term of this patent is extended or adjusted under 35 U.S.C. 154(b) by 95 days.

(21) Appl. No.: 10/378,093

(22) Filed: Mar. 3, 2003

(51) Int. Cl.⁷ ............................. A01H 5/00; A01H 5/10; A01H 1/00; C12N 5/04
(52) U.S. Cl. ...................... 800/312; 800/260; 435/415; 435/421; 435/426; 435/430; 435/430.1
(58) Field of Search ................................. 800/260, 312; 435/415, 421, 426, 430, 430.1

(56) References Cited

U.S. PATENT DOCUMENTS 6,605,755 B1 * 8/2003 Gebhardt et al. ........... 800/312

* cited by examiner

Primary Examiner—David T. Fox
(74) Attorney, Agent, or Firm—Dana S Rewoldt

(57) ABSTRACT

The present invention is in the field of soybean variety S03-95341-A98-60618 breeding and development. The present invention particularly relates to the soybean variety S03-95341-A98-60618 and its progeny, and methods of making S03-95341-A98-60618.

8 Claims, No Drawings

US 6,909,033 B1

SOYBEAN VARIETY S03-95341-A98-60618

THE FIELD OF THE INVENTION

The present invention is in the field of soybean variety S03-95341-A98-60618 breeding and development. The present invention particularly relates to the soybean variety S03-95341-A98-60618 and its progeny, and methods of making.

BACKGROUND OF THE INVENTION

The breeding and development of crops has been ongoing across the last 1000 years. The pace of this development in soybeans, as an animal foodstuff and as an oil seed has dramatically increased in the last one hundred years. Planned programs of plant breeding have increased the growth, yield and environmental hardiness of the soybean germplasm. Due to the sexual reproduction traits of the soybean the plant is basically self-pollinating. A self-pollinating plant permits pollen from one flower to be transferred to the same or another flower of the same plant. Cross-pollination occurs when the flower is pollinated with pollen from a different plant. This is a rare occurrence in nature.

Thus the growth and development of new soybean germplasm requires intervention by the breeder in the pollination of the soybean. The breeders' selections of methods of intervening in the pollination depend on the type of trait that is being selected. Soybeans are developed for a number of different types of traits morphological (form and structure), phenotypical, for growth habit, daylength temperature requirements to initiate floral or reproductive development yield. The genetic complexity of the trait drives the breeding method. Backcross breeding is employed when the cultivar that is being bred has a fairly full profile of desirable traits, but lack one or two traits that are highly inheritable. Backcrossing is often employed to move disease resistance, insect resistance and transgenes (hereinafter DNA which are introduced into the original ancestor germplasm by a transformation method) into other varieties.

When the variety is being employed to develop a new variety or an improved variety the selection methods include pedigrees, recurrent, modified and mass selection and backcrossing. Each of these selection techniques is employed with the efficiency of the breeding procedure as the driver. The breeding procedure requires a continuous evaluation of the success of the breeding program. The success is measured by yield increase, commercial appeal and environmental adaptability of the developed germplasm.

New varieties must be tested thoroughly to compare the development with the commercially available soybeans. This testing usually requires at least two years and up to six years of comparisons with other commercial soybeans. Varieties that lack the entire desirable package of traits can be used as parents in new populations for further selection. The breeding and associated testing process is 8 to 12 years' progression toward a new variety. Thousands of lines are produced and limited lines are selected in each step of the process. Thus the breeding system is like a funnel with numerous lines and selections in the first few years and fewer and fewer lines in the middle years until one line is selected for the final development testing.

The selected line or variety will be evaluated for it's the growth and development and yield. These traits of a soybean are a result of the varieties genetic potential interacting with its environment. All varieties have a maximum yield potential that is predetermined by its genetics. This hypothetical potential for yield is only obtained when the environmental conditions are perfect. Since prefect growth conditions do not exist field experimentation is necessary to provide the environmental influence and to measure its effect on the development and yield of the soybean. The breeder attempts to select for good soybean yield potential under a number of different environmental conditions.

Selecting for good soybean yield potential under a number of different environmental conditions is a process that requires planning, analysis of data in a number of seasons. Identification of the varieties that carry a superior combination of traits that provides this consistent yield potential is a complex science. Other plant traits, unusual weather patterns, diseases, and insect damage often mask the genotypic traits. One widely employed method of identifying a superior plant is to observe its performance relative to commercial and experimental plants in replicated studies. These types of studies give more certainty to the genetic potential and value of the plant.

The goal of the soybean plant breeder is to produce unique and new soybeans and progeny of the soybeans. To accomplish this the plant breeder painstakingly crosses two or more varieties or germplasm. Then the results of this cross is repeatedly selfed or backcrossed to produce new genetic patterns. Additionally, the breeder can introduce mutations into the genetic material. These can alter herbicide resistance, fatty acid compositions, and amino acid compositions of the seeds and the like. Fortunately, through transformation in combination with breeding the plant breeder can alter or introduce some genetic alleles into the breeding material.

These capabilities are widening the potential uses and markets for the various products and by-products of oil seed plants such as soybean. One of the products of soybeans is the oil of the seed. Soybean oil is employed in a number of retail products. Soybean meal is also used in food and animal feedstuffs. The traits a breeder selects for can be driven by the ultimate goals of the end user of the product. Thus if the goals of the end user is to produce an oil with a high level of oleic acid and a lower level of linoleic acid then the breeder may drive the genetics toward levels of fatty acids and accept some lesser yield potentials or other less desirable agronomic traits.

Regardless of the market characteristics of the plant most breeding proceeds along a similar path on a yearly basis. The breeder annually selects the germplasm to advance on into further development. This germplasm is grown in different locations at different altitudes, in different climates and subjected to different soil conditions. Based on the datum collected from these tests individual plants are selected during the end of the growing season. Due to the number of genes within each chromosome millions of genetic combinations exist in the breeders' experimental soybean material. This genetic diversity is so vast that a breeder cannot produce the same two cultivars twice using the exact same material. Thus the developing a single variety of useful commercial soybean germplasm is highly unpredictable, and requires intensive research.

The development of new soybeans comes through breeding techniques such as recurrent selection, mass selections, backcrossing, single seed descent and multiple seed procedure that is used to save labor costs. Other breeding methods are taught in several soybean textbooks.

The development of soybean cultivars most often requires the development of hybrid crosses (some exceptions being initial development of mutants directly through the use of the mutating agent or transformants made directly through transformation methods) and the selection of progeny therefrom. Hybrids can be achieved by manual manipulation of the sexual organs of the soybean or by the use of male sterility systems. The breeder attempts to identify true hybrids by a readily identifiable trait. These hybrids are then selected and repeatedly selfed and selected to form new homozygous lines from the heterozygous hybrids.

Outcrossing to a number of different parents creates breeding populations of fairly heterozygous populations. These populations are produced and used in pedigree breeding and recurrent selection. Pedigree breeding is commonly used with two parents which possess favorable, complementary traits. The parents are crossed to form a F1 hybrid. The progeny of the F1 hybrid is selected from this the best individuals F2 are selected; this selection process is repeated in the F3 and F4 generations. The inbreeding is carried forward and at F5–F7 the best lines are selected and tested in the development stage for potential usefulness.

Mass and recurrent selection can be used to improve populations. Several parents are intercrossed and plants are selected based on selected characteristics like superiority or excellent progeny.

In backcross breeding a genetic allele or loci is transferred into a desirable homozygous recurrent parent. The trait is in the donor parent and is tracked into the recurrent parent. The resultant plant is like the recurrent parent with the new desired allele or loci.

The single-seed descent method involves use of a segregating plant population for harvest of one seed per plant. Each seed sample is planted and the next generation is formed. When the F2 lines are advanced to F6 each plant will be derived from a different F2. The population will decline due to failure of some seeds, so not all F2 plants will be represented in the progeny.

Soybean Glycine max (L) is an important oil seed crop and a valuable field crop.

SUMMARY OF THE INVENTION

One embodiment of the invention relates to seed of a soybean cultivar designated S03-95341-A9860618. The invention relates to the plant from the seed designated S03-95341-A98-60618, or the plant parts including ovule, a tissue culture of regenerable cells, cells or protoplasts being from a tissue selected from the group consisting of leaves, pollen, embryos, meristematic cells, roots, root tips, anthers, flowers, seeds, stems and pods and pollen thereof, produced by growing the seed.

The invention in one aspect covers a soybean plant, or parts thereof, having all of the physiological and morphological characteristics of the soybean plant.

Another aspect of this invention is the soybean plant seed or derived progeny which contains a transgene (which include DNA whether or not it is a full or partial sequence) affecting herbicide resistance, insect resistance, resistance to disease, nematodes, male sterility, and altered oil or amino acids or other nutritional quality.

The present invention further covers a method for producing a soybean seed with the steps of crossing at least two parent soybean plants and harvesting the hybrid soybean seed, wherein at least one parent soybean plant is the present invention. In another aspect of the invention covers the hybrid soybean seed and the progeny soybean plant and resultant seed, or parts thereof from the hybrid seed or plant or its progeny.

In an additional aspect the invention covers a method for producing a soybean progeny from the invention by crossing soybean line S03-95341-A98-60618 with a second soybean plant to yield progeny soybean seed and then growing progeny soybean seed to develop a derived soybean line.

Yet another aspect of the invention covers a method for a breeding program using plant breeding techniques which employ the soybean plant S03-95341-A98-60618 as plant breeding material and performing breeding by selection techniques, backcrossing, pedigree breeding, marker enhanced selection, mutation and transformation.

| Soybean Data Collection | | | | |
|---|---|---|---|---|
| Core Traits | Abbr. | Description | Timing | Scale |
| Hila | HC | Phenotypic color; All experiments. | | G = Gray; BR = Brown; IB = Imperfect Black; Bl = Black; Y = Yellow; BF = Buff; IY = Imperfect Yellow; X = Mix |
| Flower | FC | Phenotypic color; All experiments. | | W = White; P = Purple; X = Mix |
| Pod | POD | Phenotypic color; All experiments. | | T = Tan; B = Brown; X = Mixed |
| Pubescence | PUB | Phenotypic color; All experiments. | | G = Gray; T = Tawny; LT = Light Tawny; X = Mixed |
| GWT | GWT | Grain weight/plot | Harvest | Pounds |
| H2O | H20 | Grain moisture/plot | Harvest | % moisture |
| Necessary Traits | Abbr. | | Timing | Scale |
| Hypocotyl Elongation | HYPO | Replicated Nursery | May to June | 1 to 5 (1 = best) |
| Seedling Establishment | EMG | 4 locations/test | VE–V1 | 1 to 5 (1 = best) |

-continued

| Soybean Data Collection | | | | |
|---|---|---|---|---|
| Maturity | MAT | 4 locations/test | | Taken in days after Aug. 31 |
| Plant Height | PLTHT | 4 locations/test | Harvest | Taken in inches |
| Branching | BR | 4 locations/test | R8–Harvest | 1 to 5 (1 = no branch) |
| Agronomic Traits | Abbr. | Opportunistic | Timing | Scale |
| Green Lodging | GLOD | Where differential occurs. | R5 to R6 | 1 = All erect<br>2 = 67°<br>3 = 45°<br>4 = 22°<br>5 = 0°  |
| Stem Lodging | LOD | Where differential occurs | Harvest | 1 = All erect<br>2 = 67°<br>3 = 45°<br>4 = 22°<br>5 = 0°  |
| Shatter | SHAT | Where differential occurs | Harvest | 1 to 5 (1 = best) |
| Opportunistic Disease Ratings | Abbr. | Key Maturities | | Scale |
| Phytophthora Root Rot | PFT | All | | 1 to 5 (1 = best) |
| Brown Stem Rot | BSR | G0 to EGIII | | 1 to 5 (1 = best) |
| Sclerotinia White Mold | SWM | G0 to EGIII | | 1 to 5 (1 = best) |
| Sudden Death Syndrome | SDS | EGIII to GVII | | 1 to 5 (1 = best) |
| Stem Canker | STMC | MGII to GVII | | 1 to 5 (1 = best) |
| Charcoal Rot | CROT | LGIII to GVII | | 1 to 5 (1 = best) |
| Frog Eye | FROG | EGIII to GVII | | 1 to 5 (1 = best) |
| Disease Nurseries | Abbr. | Path | Timing | Scale |
| Iron Deficiency Chlorosis | IDC | Internal Field Nursery | June–July | 1 to 5 (1 = best) |
| Soybean Cyst Nematode | SCN | Race 3 Internal Nursery | Nov–April 30d cycle | # = the race<br>R3 is resistant to race 3<br>MR14 is moderately resistant to race 14<br>R–MR–MS–S<br>R = resistant<br>S = susceptible<br>M = moderately |
| Phytophthora Root Rot PRR | PFT or PGR | | | 1 to 5 (1 = best)<br>for field tolerance and resistance<br>gene Rps 1a, Rps 1b, Rps 1c,<br>Rps 1k, etc for specific genes.<br>Disease Severity Index or DSI. |
| Sudden Death Syndrome | SDS | | | 1 to 5 (1 = best) |
| Brown Stem Rot | BSR | | | R–MR–MS–S |
| Root Knot Nematode | RKN | | | R = resistant<br>S = susceptible<br>M = moderately |
| Stem Canker | STMC | | | 1 to 5 (1 = best) |
| Herbicide Evalutation | Abbr. | | | |
| Sulfentraxone | SULF | | | Sensitive, Tolerant |
| Metributzin | MET | | | Sensitive, Tolerant |

***All data to default to a "." (period) when data is not observed

DETAILED DESCRIPTION

Trait Definitions

Hypocotyl Elongation (HYPO) A rating of a variety's hypocotyl extension after germination when planted at a 5" depth in sand and maintained a warm germination environment for 10 days.

Seedling Establishment (EMG) A rating of the uniform establishment and growth of seedlings.

Maturity (MAT) The number of days after Aug. 31 when 95% of the main stem pods in the plot have reached their mature color.

Peroxidase Activity (Perox)—seed protein peroxidase activity is defined as a chemical taxonomic technique to separate cultivars based on the presence or absence of the peroxidase enzyme in the seed coat. Ratings are POS= positive for peroxidase enzyme or NEG=negative for peroxidase enzyme.

Plant Height (PLTHT) The average measured plant height in inches.

Branching (BRANCH) Rating of the number of branches and their relative importance to yield. Taken at growth expressive locations.

Green Lodging (GLODGE) Rating based on the average of plants leaning from vertical in R5 to R6 stage.

Stem Lodging (LODGE) Rating based on the average of plants leaning from vertical at harvest.

Shatter (SHAT) Rating of pre-harvest loses based on amount of plants with open pods.

Iron Deficiency Chlorosis (IDC) A composite rating of Yellow Flash, Green-up, and Stunting in HpH soil.

Phytophthora Root Rot (PGR) or (PFT) Greenhouse pot—root dip method for PFT and hypodermic needle method for rating PGR.

Root Knot Nematode (RKN) Greenhouse screen—30 day screen using infested soil. Rating Scale based upon female reproduction index on a susceptible check set where <10%=R; <30%=MR; <60%=MS; >60%=S.

Stem Canker (STC) Based on number of lesions, scale 1–5.

Sulfentrazone (SULF) Authority™ (commercial herbicide) Greenhouse nursery rating damage of multiple rates.

Metributzin (MET) Greenhouse nursery rating damage of multiple rates.

Definitions of Staging of Development

The plant development staging system employed divides stages as vegetative (V) and reproductive (R). This system accurately identifies the stages of a soybean plant. However, all plants in a given field will not be in the stage at the same time. Each specific V or R stage is defined as when 50% or more of the plants in the field are in or beyond that stage.

The first two stages of V are designated a VE (emergence) and VC (cotyledon stage). Subdivisions of the V stages are then designated numerically as V1, V2, V3 through V (n) The last V stage is designated as V (n), where (n) represents the number for the last node stage of the specific variety. The (n) will vary with variety and environment. The eight subdivisions of the reproductive stages (R) states are also designated numerically. R1=beginning bloom; R2=full bloom; R3=beginning pod; R4=full pod; R5=beginning seed; R6=Full Seed; R7=beginning maturity; R8=Full maturity.

BROWN STEM ROT (BSR)-This disease is caused by the fungus *Phialophora gregata*. The disease is a late-season, cool-temperature, soilborne which in appropriate favorable weather can cause up to 30 percent yield losses in soybean fields. For purposes of these tests the information is gathered in a greenhouse with a plant in a pot then a root dip procedure is employed.

SUDDEN DEATH SYNDROME (SDS)—This disease is caused by slow-rowing strains of *Fursarium solani* that produce bluish pigments in culture. The disease is mid- to late season soil borne and occurs in soybean fields with high yield potential. Yield losses may be total/severely affected fields. Sudden Death Syndrome (SDS) is based on leaf area affected, scale used for these tests is 1–5.

SOYBEAN CYST NEMATODE—The Soybean Cyst Nematode (SCN) *Heterodera glycines*, is a small plant-parasitic roundworm that attacks the roots of soybeans.

Soybean Cyst Nematode (SCN) for purposes of these tests are done as a greenhouse screen—30 day screen using infested soil. Rating Scale based upon female reproduction index on a susceptible check set where <10%=R; <30%=MR; <60%=MS; >60%=S. In priority order, the screening races include: 3, 14, & 1.

MATURITY DATE. Plants are considered mature when 95% of the pods have reached their mature color. The number of days is either calculated from September 1 or from the planting date. (MR#) wherein # equals days.

RELATIVE MATURITY GROUP (RM). Industry Standard for varieties groups, based day length or latitude. Long day length (northern areas in the Northern Hemisphere) are classified as (Groups 000,00,0,) and extend to very short day lengths variety groups (southern areas in Northern Hemisphere) classified as (Groups VII,VIII, IX).

SEED YIELD (Bushels/Acre). The yield in bushels/acre is the actual yield of the grain at harvest.

SPECIFICATION AMENDMENT

SHATTERING. The rate of pod dehiscence prior to harvest. Pod dehiscence involves beans dropping out of the pods. Shatter (SHAT) for these tests the rating of pre-harvest loses is based on amount of plants with open pods.

PLANT. Means the plant, the plant's cells, plant protoplasts, plant cells of tissue culture from which soybean plants can be regenerated, plant calli, plant clumps, and plant cells that are intact in plants or parts of the plants, such as pollen, nodes, roots, flowers, seeds, pods, leaves, stems, and the like.

The present invention is 95341-A98-60618. This soybean is developed for its use of the beans. 95341-A98-60618 is a 2.9 relative maturity. 95341-A98-60618 is adapted to both wide and narrow row spacing in the late group 2 maturities. This variety is an excellent choice for high performance and provides excellent brown stem rot resistance. This line is growth and is adaptable to moisture stress. This cultivar's general area of adaptation in the U.S. includes most soil types found in Northern to Central Nebraska, Northern Illinios, Central Iowa, Northern Indiana.

The traits of the invention are listed below.

| Trait | |
| --- | --- |
| RM | 2.9 |
| HR-herbicide resistance | — |
| Flower Color | P |
| Pubescene Color | T |
| Pod Color | [T] B |
| Hila Color | BL |
| Lust | Dull |
| Perox | NEG |
| PFT | 4.0 |
| Hypo | 2.00 |
| IDC | 3.7 |
| BSR | 1.7 |
| SDS | 2.0 |

The instant invention provides methods and composition relating to plants, seeds and derivatives of the soybean cultivar S03-95341-A98-60618. Soybean cultivar S03-95341-A98-60618 has superior characteristics. The S03-95341-A98-60618 line has been selfed sufficient number of generations to provide a stable and uniform plant variety.

Cultivar S03-95341-A98-60618 shows no variants other than expected due to environment or that normally would occur for almost any characteristic during the course of repeated sexual reproduction. Some of the criteria used to select in various generations include: seed yield, lodging resistance, emergence, appearance, disease tolerance, maturity, plant height, maturity and shattering data.

The inventor believes that S03-95341-A98-60618 is similar to the comparison varieties. However, as shown in the tables, S03-95341-A98-60618 differs from these cultivars.

Direct comparisons were made between S03-95341-A98-60618 and these competing commercial varieties. Traits measured included yield, maturity, moisture, lodging, plant height, field emergence, protein and oil. The results of the comparison are presented in below. The number of tests in which the varieties were compared is shown. The deviation or difference of the results, T-value and the traits which showed a significant difference and the level of that significance are in the first table. The second table indicates the advantage (positive number) or disadvantage (negative number) of the present invention when compared to the commercial lines.

The present invention S03-95341-A98-60618 can carry genetic engineered recombinant genetic material to give improved traits or qualities to the soybean. For example, but not limitation, the present invention can carry, the glyphosate resistance gene for herbicide resistance as taught in the Dekalb U.S. patent or STS mutation for herbicide resistance. Additional traits carried in transgenes or mutation can be transferred into the present invention. Some of these genes include genes that give disease resistance to sclerotina such as the a oxalate oxidase (Ox Ox) gene as taught in PCT/FR92/00195 Rhone Polunc and/or an Ox Decarboxylate gene for disease resistance or genes designed to alter the soybean oil within the seed such as desaturase genes or genes designed to alter the soybean's amino acid characteristics. This line can be crossed with another soybean line which carries a gene that acts to provide herbicide resistance or alter the saturated and/or unsaturated fatty acid content of the oil within the seed, or the amino acid profile of the seed.

The present invention S03-95341-A98-60618 is employed in a number of plot repetitions to establish trait characteristics.

| External Name | RM | Flower | Hilum | BSR | SDS | IDC |
|---|---|---|---|---|---|---|
| S03-95341-A98-60618 | 2.9 | P | BL | 1.7 | 2.0 | 3.7 |
| A2553 | 2.5 | — | IB | | 2.0 | 3.5 |
| P93B15 | 3.1 | P | BR | | | 4.9 |
| S30-Y8 | 3 | P | IB | | 1.0 | 4.0 |

HR=herbicide resistance
RR=glyphosate resistance from Monsanto

The traits of the present invention differ from the comparison commercial soybean lines in a combination of a number of traits. The present invention shows a different hilum than each of the other lines. The present invention has nice brown stem root resistance and carries some levels of tolerance to Sudden Death Syndrome. Additionally the present invention shows better IDC ratings than does any of the other commercial lines except A2553.

The present invention S03-95341-A98-60618 is employed in a trialling for a number of characteristics. These tests allow the usefulness of the invention to be shown in light of the environmental genetic interactions.

| Ent | Yld | Moist | Appearance | Branch |
|---|---|---|---|---|
| S03-95341-A98-60618 vs A2553 | | | | |
| S03-95341-A98-60618 | 65.3 | 11.7 | 2 | 2.8 |
| A2553 | 61.7 | 11.7 | 2.4 | 3.1 |
| # LOCS | 15 | 15 | 5 | 2 |
| Diff | 3.6 | 0 | −0.4 | −0.4 |
| Std | 7.6 | 0.3 | 1.1 | 0.5 |
| T-val | 1.84 | 0.02 | −0.78 | −1 |
| Prob | 0.086* | 0.986 | 0.477 | 0.5 |
| S03-95341-A98-60618 vs P93B15 | | | | |
| S03-95341-A98-60618 | 65.3 | 11.7 | 2 | 2.8 |
| P93B15 | 66.1 | 11.6 | 2 | 3.6 |
| # LOCS | 15 | 15 | 5 | 2 |
| Diff | −0.8 | 0.1 | 0 | −0.9 |
| Std | 8.1 | 0.1 | 0 | 0.2 |
| T-val | −0.38 | 1.99 | | −7 |
| Prob | 0.712 | 0.067* | | 0.090* |
| S03-95341-A98-60618 vs S30-Y8 | | | | |
| S03-95341-A98-60618 | 65.3 | 11.7 | 2 | 2.8 |
| S30-Y8 | 63.9 | 11.8 | 2.1 | 3.6 |
| # LOCS | 15 | 15 | 5 | 2 |
| Diff | 1.4 | −0.1 | −0.1 | −0.9 |
| Std | 7.3 | 0.3 | 0.9 | 0.2 |
| T-val | 0.74 | −1.89 | −0.25 | −7 |
| Prob | 0.41 | 0.080* | 0.815 | 0.090* |

*Significant at the 0.10 level
**Significant at the 0.05 level
***Significant at the 0.01 level
Moist = Moisture
Yld = Yield

| Ent | BSR | Emergence | Lg | Mat |
|---|---|---|---|---|
| S03-95341-A98-60618 vs A2553 | | | | |
| S03-95341-A98-60618 | | 2 | 1.5 | 20.5 |
| A2553 | | 2.3 | 1.7 | 17.1 |
| # LOCS | 0 | 2 | 9 | 7 |
| Diff | | −0.3 | −0.2 | 3.3 |
| Std | | 0.4 | 0.4 | 3.3 |
| T-val | | −1 | −1.15 | 2.69 |
| Prob | | 0.5 | 0.282 | 0.036** |
| S03-95341-A98-60618 vs P93B15 | | | | |
| S03-95341-A98-60618 | | 2 | 1.5 | 20.5 |
| P93B15 | | 2.5 | 1.7 | 22.9 |
| # LOCS | 0 | 2 | 9 | 7 |
| Diff | | −0.5 | −0.2 | −2.4 |
| Std | | 0 | 0.4 | 2.3 |
| T-val | | | −1.15 | −2.78 |
| Prob | | | 0.282 | 0.032** |
| S03-95341-A98-60618 vs S30-Y8 | | | | |
| S03-95341-A98-60618 | | 2 | 1.5 | 20.5 |
| S30-Y8 | | 1.7 | 1.3 | 21.5 |
| # LOCS | 0 | 2 | 9 | 7 |
| Diff | | 0.3 | 0.2 | −1 |
| Std | | 0.3 | 0.4 | 2.9 |
| T-val | | 1.26 | 1.44 | −0.93 |
| Prob | | 0.427 | 0.189 | 0.388 |

Lg = lodging
Mat = maturity in days after September 1

| Ent | Pltht | PRR | Shatter | IDC |
|---|---|---|---|---|
| S03-95341-A98-60618 vs A2553 | | | | |
| S03-95341-A98-60618 | 35.7 | | | 4.4 |
| A2553 | 32.6 | | | 4 |
| # LOCS | 5 | 0 | 0 | 4 |
| Diff | 3.1 | | | 0.5 |

-continued

| Ent | Pltht | PRR | Shatter | IDC |
|---|---|---|---|---|
| Std | 3 | | | 0.5 |
| T-val | 2.27 | | | 1.94 |
| Prob | 0.085* | | | 0.147 |
| S03-95341-A98-60618 vs P93B15 | | | | |
| S03-95341-A98-60618 | 35.7 | | | 4.4 |
| P93B15 | 33.6 | | | 4.6 |
| # LOCS | 5 | 0 | 0 | 4 |
| Diff | 2.1 | | | −0.2 |
| Std | 2.2 | | | 0.2 |
| T-val | 2.09 | | | −1.57 |
| Prob | 0.105 | | | 0.215 |
| S03-95341-A98-60618 vs S30-Y8 | | | | |
| S03-95341-A98-60618 | 35.7 | | | 4.4 |
| S30-Y8 | 34.4 | | | 4.6 |
| # LOCS | 5 | 0 | 0 | 4 |
| Diff | 1.3 | | | −0.1 |
| Std | 2.9 | | | 0.3 |
| T-val | 1.03 | | | −0.93 |
| Prob | 0.36 | | | 0.423 |

Pltht = plant height

The present invention is providing yield and moisture consistent with the comparison commercial lines. Each of these lines have their own positive traits. Each of these lines are different from the present invention. The lodging levels of the present invention in comparison to the other lines very similar without any significant difference. The IDC rating is slightly lower than two of the other lines though not significantly lower than the commercial lines. The yield and other data is a snapshot of each of these lines' results in the specific environment and will differ when other environmental interactions are measured. The present invention is being compared with lines of similar maturities which are quite like the maturity of the present invention. The maturity is measured in the number of days after September 1 until maturity is reached.

This S03-95341-A98-60618 invention was compared with the comparison soybean product for certain grain quality traits. The data in the first column shows that seed per pound of the present invention are similar to A2553 but different from S30-Y8. The protein levels found in the present invention are consistently higher in these results. The oil level in the seed of the present invention is on the lower side comparatively.

| | sds per lb | Protein | oil |
|---|---|---|---|
| S03-95341-A98-60618 | 3100–3900 | 34.00 | 18.60 |
| A2553 | 3000–4100 | 33.20 | 19.00 |
| S30-Y8 | 3100–3600 | 33.00 | 18.70 |

This invention also is directed to methods for producing a new soybean plant by crossing a first parent plant with a second parent plant wherein the first or second parent plant is the present invention. Additionally, the present invention maybe used in the variety development process to derive progeny in a breeding population or crossing. Further, both first and second parent plants can come from the soybean line S03-95341-A98-60618. A variety of breeding methods can be selected depending on the mode of reproduction, the trait, the condition of the germplasm. Thus, any such methods using the S03-95341-A98-60618 are part of this invention: selfing, backcrosses, recurrent selection, mass selection and the like.

Transformation methods are means for integrating new genetic coding sequences (transgenes) into the plant's genome by the incorporation of these sequences into a plant through man's assistance. Many dicots including soybeans can easily be transformed with Agrobacterium. The most common method of transformation after the use of agrobacterium is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art. The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular are well known in the art. The plants from the transformation process or the plants resulting from a cross using a transformed line or the progeny of such plants are transgenic plants that carry the transgene.

Deposit Information

A deposit of the Advanta USA, Inc. Seed soybean cultivar S03-95341-A98-60618 disclosed above and recited in the appended claims will be made with the American Type Culture Collection (ATCC), 10801 University Blvd., Manassas, Va. 20110. The date of deposit was Nov. 24, 2004. The deposit of 2,500 seeds maintained by Advanta USA, Inc. since prior to the filing date of this application. All restrictions on the deposit upon issuance of the patent will be removed, and the deposit is intended to meet all of the requirements of 37 C.F.R. §§ 1.801–1.809. The ATCC accession number is PTA-6331. The viability of the deposit was positive in tests ran on Dec. 1, 2004. The deposit will be maintained in the depository for a period of 30 years, or 5 years after the last request, or for the effective life of the patent, whichever is longer, and will be replaced as necessary during that period.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. A soybean seed designated S03-95341-A98-60618, representative seed of said soybean variety S03-95341-A98-60618 having been deposited under ATTC Accession No. PTA-6331.

2. A soybean plant, or a part thereof, produced by growing the seed of claim 1.

3. The soybean plant part of claim 2 wherein said part is pollen.

4. The soybean plant part of claim 2 wherein said part is an ovule.

5. A tissue culture of protoplasts or regenerable cells from the plant of claim 2.

6. The tissue culture according to claim 5, the cells or protoplasts of the tissue culture are obtained from plant tissues selected from the group consisting of: leaf, pollen, cotyledon, hypocotyls, embryos, root, pod, flower, shoot and stalk.

7. A soybean plant regenerated from the tissue culture of claim 5, having all the morphological and physiological characteristics of soybean variety S03-95341-A98-60618, representative seed of said soybean variety S03-95341-A98-60618 having been deposited under ATCC Accession No. PTA-6331.

8. A method for producing a progeny soybean plant comprising crossing the plant of claim 2 with second soybean plant, harvesting the resultant soybean seed, and growing a progeny soybean plant.

* * * * *